(12) United States Patent
Lawson

(10) Patent No.: US 6,277,120 B1
(45) Date of Patent: Aug. 21, 2001

(54) CABLE-ANCHOR SYSTEM FOR SPINAL FIXATION

(76) Inventor: Kevin Jon Lawson, 2662 Edith Ave., Redding, CA (US) 96001

( * ) Notice: Subject to any disclaimer, the term of this patent is extended or adjusted under 35 U.S.C. 154(b) by 0 days.

(21) Appl. No.: 09/665,603

(22) Filed: Sep. 20, 2000

(51) Int. Cl.⁷ .................................................. H61B 17/56
(52) U.S. Cl. ................................................. 606/61; 606/74
(58) Field of Search .................................. 606/61, 60, 72, 606/64, 69, 70, 71, 73; 623/17.11, 17.16

(56) References Cited

U.S. PATENT DOCUMENTS

| | | | |
|---|---|---|---|
| 4,003,376 | * | 1/1977 | McKay et al. .......................... 606/61 |
| 4,570,618 | * | 2/1986 | Wu ......................................... 606/61 |
| 5,030,220 | | 7/1991 | Howland ................................ 606/61 |
| 5,116,340 | | 5/1992 | Songer et al. ......................... 606/103 |
| 5,190,545 | * | 3/1993 | Corsi et al. ............................ 606/74 |
| 5,304,178 | | 4/1994 | Stahurski .............................. 606/61 |
| 5,632,744 | * | 5/1997 | Campbell, Jr. ........................ 606/61 |
| 5,662,653 | | 9/1997 | Songer et al. ......................... 606/61 |
| 5,772,663 | | 6/1998 | Whiteside et al. .................... 606/74 |
| 5,800,433 | | 9/1998 | Benzel et al. ......................... 606/61 |
| 5,989,250 | | 11/1999 | Wagner et al. ........................ 606/61 |
| 6,030,389 | | 2/2000 | Wagner et al. ........................ 606/71 |
| 6,053,921 | | 4/2000 | Wagner et al. ........................ 606/74 |
| 6,086,590 | * | 7/2000 | Margulies et al. .................... 606/61 |

* cited by examiner

*Primary Examiner*—Pedro Philogene
(74) *Attorney, Agent, or Firm*—Robert Charles Hill

(57) ABSTRACT

A spinal-fixation system comprises a dual parallel bridging that runs along a posterior length of the spine and is anchored with cables looped through a dorsal corner of the spinal canals of respective adjacent vertebrae.

11 Claims, 4 Drawing Sheets

Fig. 1A
Fig. 1B
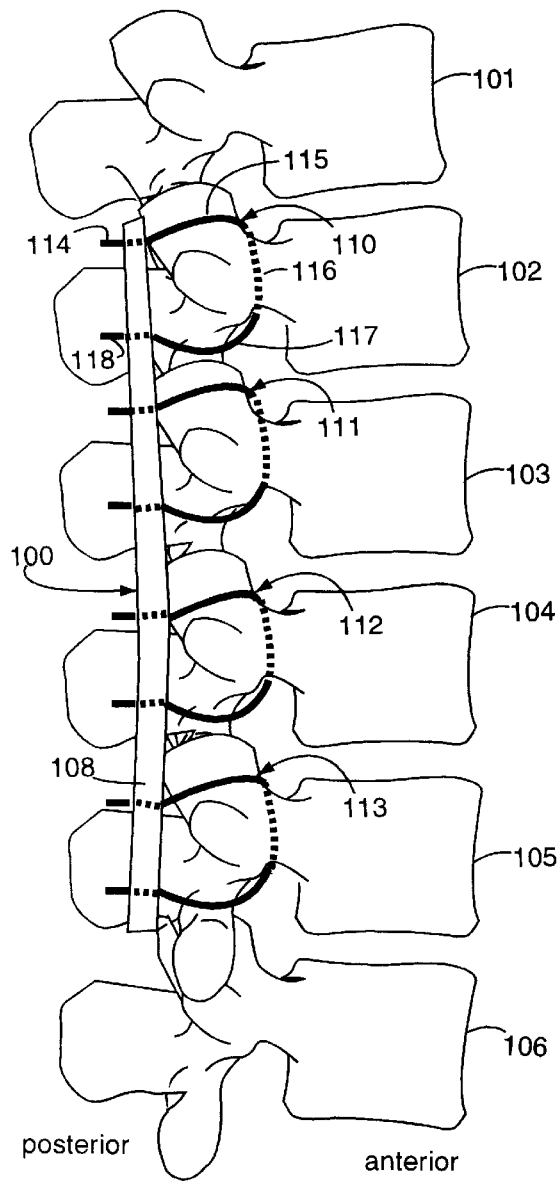
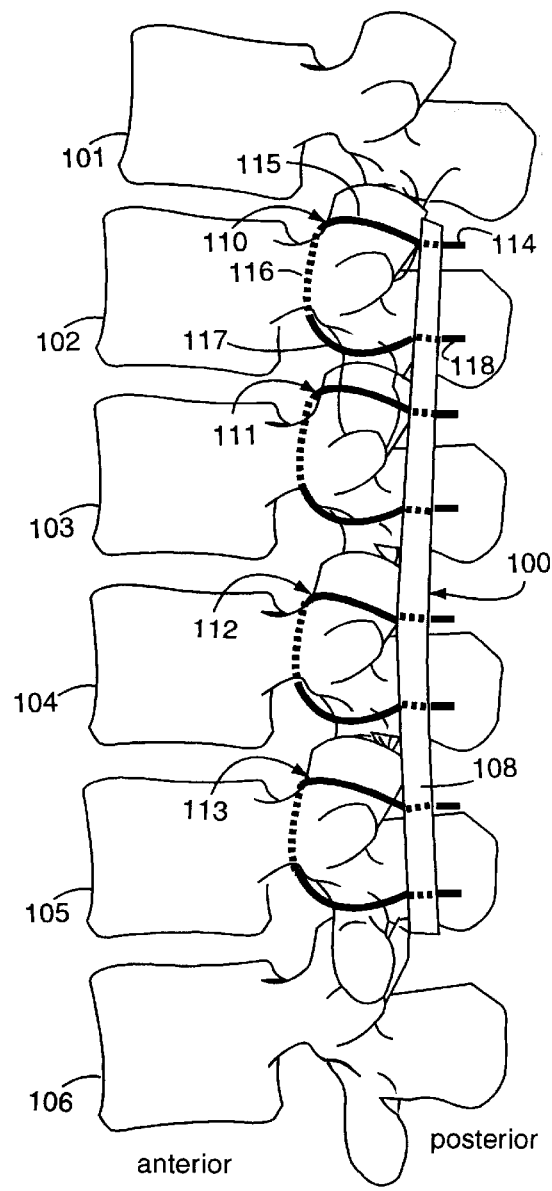

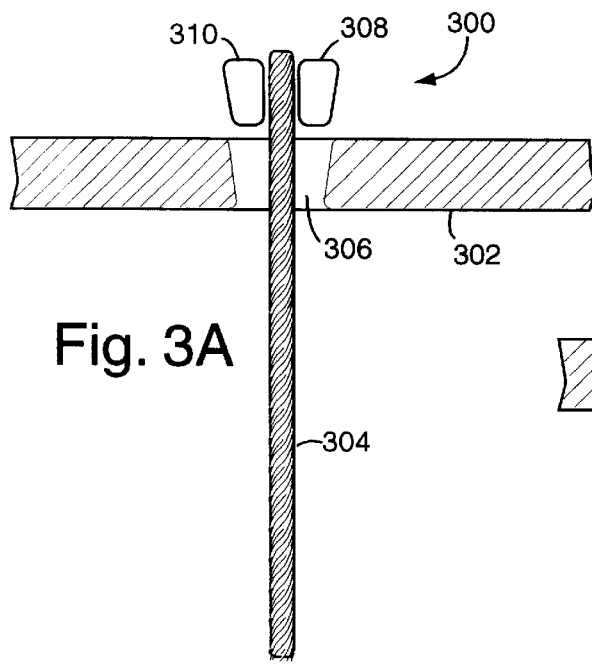
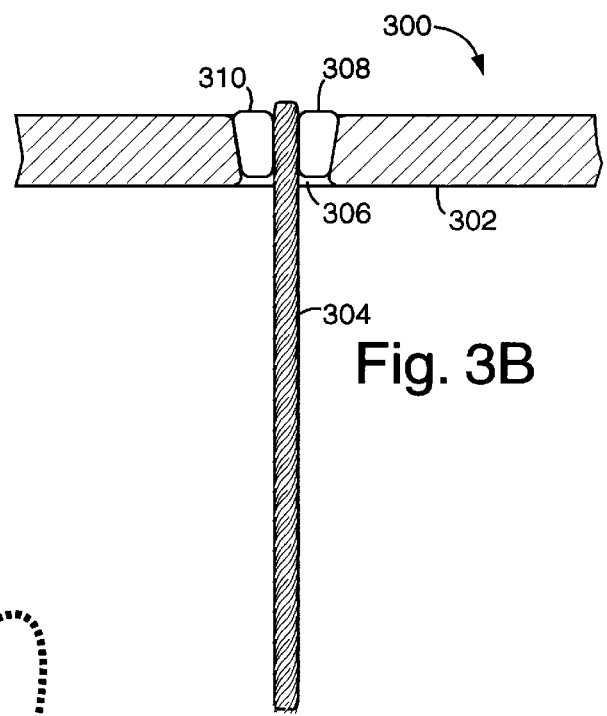
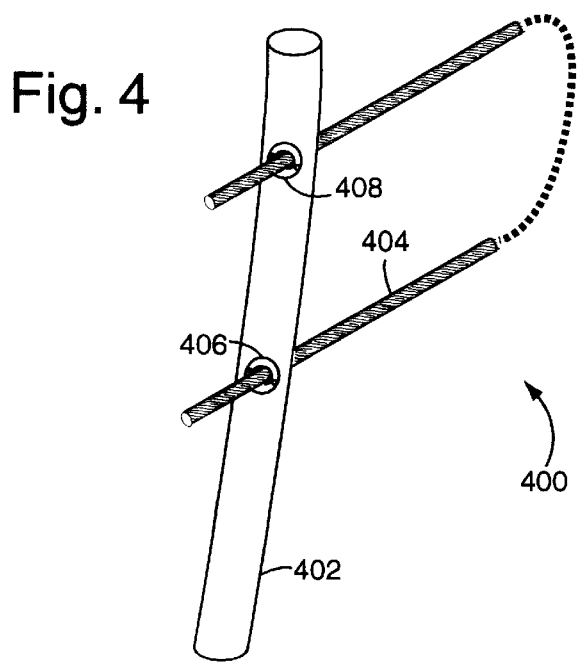

CABLE-ANCHOR SYSTEM FOR SPINAL FIXATION

BACKGROUND OF THE INVENTION

1. Field of the Invention

The present invention relates to surgical methods and devices to stabilize vertebra, and more particularly to plates and rods anchored by cables for immobilizing human spine vertebrae.

2. Description of Related Art

Degenerative disc disease accounts for more than 100,000 low back spinal fusion procedures in the United States annually, according to Columbia, Colo. hospitals. The intervertebral disc is a pad of cartilage-type material situated between spinal bones. Each disc serves as a connector, spacer, and shock absorber for the spine. A soft, jelly-like center is contained by outer layers of fibrous tissue. Healthy discs help allow normal turning and bending. Trauma or injury to the spine can cause discs to tear, bulge, herniate, and even rupture. This can be quite painful, as the soft center of the disc leaks, putting pressure on the adjacent nerve roots and spinal cord.

A damaged disc can cause nerve dysfunction and debilitating pain in the back, legs and arms. Typical treatments that provide relief and allow patients to function again include back braces, medical treatment, physical therapy and surgery to remove the disc. A conventional surgical solution removes the bad disc and promotes new bone growth in the space to fuse the adjacent vertebrae together.

One conventional approach implants one or more metal rods to bridge across a damaged portion of the spine. Such rods lock the bridged-over spinal vertebrae so they cannot twist or flex on their intervertebral discs. In some cases, such discs may have been removed and the object of the spinal fixation is to promote bone growth that fuses the vertebrae together. Such a system is described by Erik Wagner, et al., in U.S. Pat. No. 5,989,250, issued Nov. 23, 1999. Bone hooks and bone screws secured to individual vertebrae serve as anchors for a bridging spinal-rod. The rods are dressed to follow along the lamina inside the two parallel canals formed by the posterior spinous processes of each vertebrae. A similar system is described by Robert Howland in U.S. Pat. No. 5,030,220, issued Jul. 9, 1991.

DePuy AcroMed, a subsidiary of Johnson & Johnson, markets several spinal-fixation systems and devices. For example, the ISOLA Spinal System is a rod-based, thoracic and lumbar multi-level fixation system. Dr. Kiyoshi Kaneda's Anterior Spine Stabilization System is another that is universally used for tumor and trauma spinal fixation. The ACROMED Cable System by Matthew Songer, MD, uses multi-strand cable for cervical, thoracic and lumbar fixation. The ACROPLATE Anterior Cervical System uses a titanium plate on the cervical anterior, and is secured with bi-cortial screws.

Edward Benzel, et al., describe a spinal column retainer in U.S. Pat. No. 5,800,433, issued Sep. 1, 1998. A pair of parallel fenestrated support rods are secured to each vertebrae with a middle plate. A number of holes in each plate allow bone screws to be used to secure the plate to the respective vertebrae. Such plates do not span between vertebrae, the rods do that. Set screws in the plates allow the plates to be locked to each rod, and thus will resist twisting and/or sliding.

Erik Wagner, et al., also describe in U.S. Pat. No. 6,030,389, issued Feb. 29, 2000, a bone plate device for human spine stabilization. Such plates are anchored with bone screws that are angled to one another so that they will bed deeply into the strongest bone material.

A direct rod-to-bone attachment screw is described by Robert Songer, et al., in U.S. Pat. No. 5,662,653, issued Sep. 2, 1997. A bone screw resembling an eye-bolt is screwed into the vertebrae and fenestrated support rod is threaded through the eye-loops. Clamps in the eye-loops open to receive the rods and lock them within.

All such bone screw dependent systems suffer from screw breakout and screw backout problems. Various ingenious techniques and devices have been developed to mitigate these problems, but cable-anchored approaches seem to be superior.

Some prior-art spinal-fixation systems pass loops of heavy cable or wire under the spinal lamina and through the spinal canal. This, of course, must be done without disturbing the nerves or spinal cord. There is a little spare room in the spinal canal not required by the spinal cord. Each thoracic vertebrae in the back, for example, has a vertebral canal with a small space in the posterior (dorsal) corner, adjacent to the lamina. There a cable can be safely passed through. But just forward of this is the spinal cord which is very delicate and absolutely cannot tolerate being squeezed or disturbed.

A surgical cable system and method is described by Erik Wagner, et al., in U.S. Pat. No. 6,053,921, issued Apr. 25, 2000. A metal crimp or collet is used to secure a cable in a loop. A tensioning device allows the cable to be tightened around vertebral bone.

The anchor wires of prior art spinal-fixation systems are conventionally twisted around opposite ends and the fenestrated support rods. Such can easily slip and twist on the usually smooth rods. The alternative anchor cables are multi-strand wires that cannot simply be twisted together. Various cable clamps and locks have been marketed commercially to secure such cables to the rods. A bone-banding cable is described by Leo Whiteside, et al., in U.S. Pat. No. 5,772,663, issued Jun. 30, 1998.

Once a cable has been passed, a device can be used to secure the cables like that described by Robert J. Songer, et al., in U.S. Pat. No. 5,116,340, issued May 26, 1992. Surgical cables looped through spinal vertebrae are conventionally secured by Songer crimping pliers.

All the United States Patents cited herein are incorporated by reference. Such Patents themselves cite many prior art patents and technical documents that will assist the reader in understanding and implementing embodiments of the present invention. These are lodged in the file wrappers of those Patents.

What is needed is a spinal-fixation system that combines thoracic and lumbar posterior plates or bars anchored with cables or wires that individually pass through the spinal canals of adjacent vertebrae.

SUMMARY OF THE INVENTION

An object of the present invention is to provide a spinal-fixation system for immobilizing at least two adjacent thoracic or lumbar vertebrae.

Another object of the present invention is to provide a spinal-fixation system anchored with cables or wires that pass through the spaces of the spinal canal of adjacent vertebrae.

Briefly, a spinal-fixation system embodiment of the present invention comprises a dual parallel bridging that runs along a posterior length of the spine and is anchored with cables looped through a dorsal corner of the spinal canals of respective adjacent vertebrae.

An advantage of the present invention is that a spinal-fixation system is provided that securely immobilizes the spine of a patient.

Another advantage of the present invention is that a spinal-fixation system is provided that makes it safer and easier for a surgeon to immobilize damaged portions of the spine.

The above and still further objects, features, and advantages of the present invention will become apparent upon consideration of the following detailed description of specific embodiments thereof, especially when taken in conjunction with the accompanying drawings.

BRIEF DESCRIPTION OF THE DRAWINGS

FIGS. 1A and 1B are right and left side diagrams representing the spine of a patient having a spinal implant embodiment of the present invention;

FIGS. 3A and 3B are partial cross-sectional diagrams of an embodiment of the present invention that attaches anchoring cables directly to fenestrated support rods;

FIG. 4 is a perspective diagram of a spinal fixation system similar to that of FIGS. 3A and 3B;

DETAILED DESCRIPTION OF THE INVENTION

Figure 2:
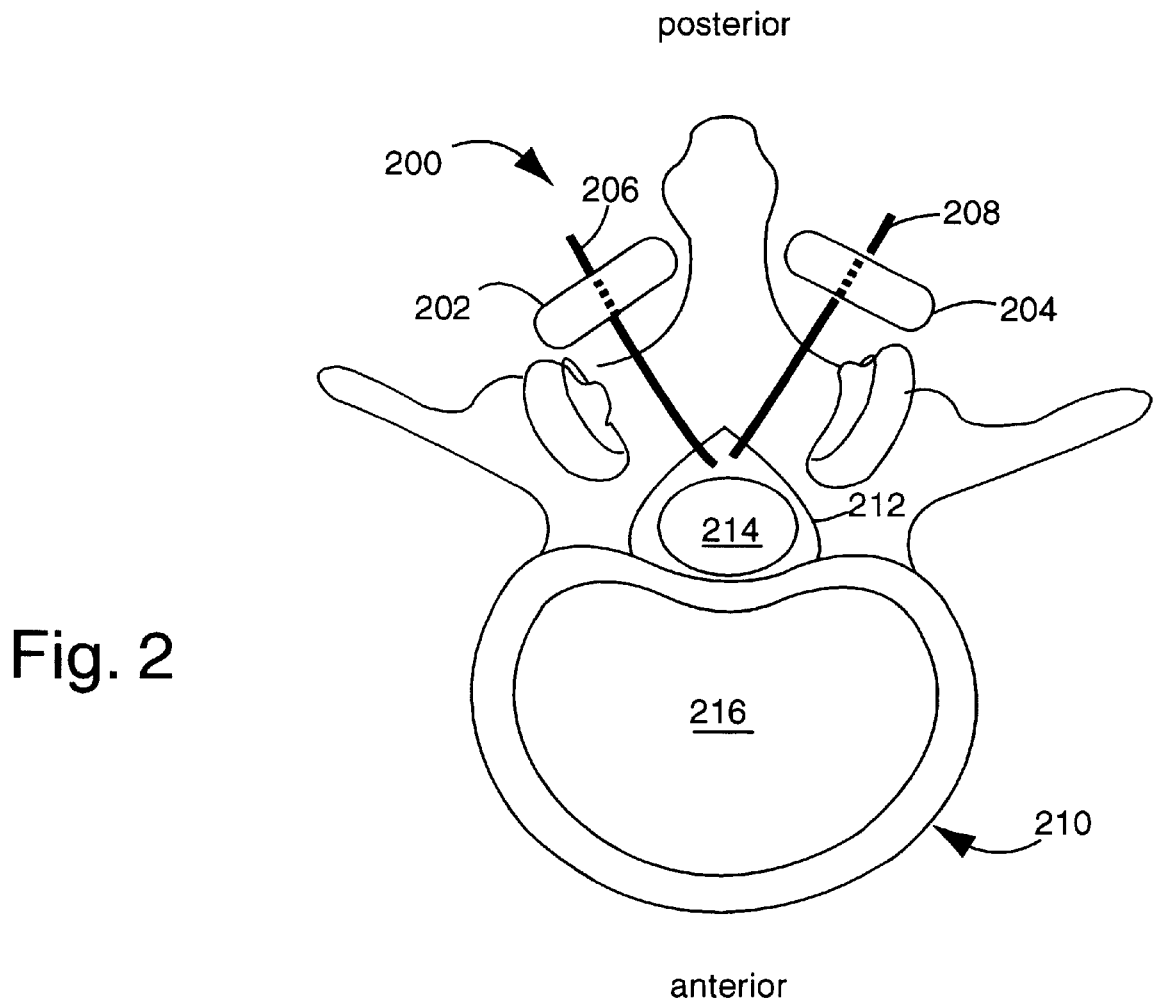
FIG. 2 is a cross-sectional view of a stabilization implant embodiment of the present invention similar to that shown in FIG. 1.

FIGS. 1A and 1B illustrate a spinal-fixation system embodiment of the present invention, and is referred to herein by the general reference numeral 100. The spinal-fixation system 100 immobilizes portions of the human L1–L5 lumbar vertebrae and T1–T12 thoracic vertebrae as represented by a series of vertebrae 101–106. C1–C7 is also feasible. In FIG. 1, it is assumed that vertebrae 102–105 are to be immobilized relative to one another. As few as two adjacent such vertebrae could be immobilized by the system 100, e.g., to promote intervertebral bone-fusion growth. FIG. 1A shows only the right-side half of the preferred system, and FIG. 1B shows the left-side half. The corresponding elements in each half are interchangeable, and so they are numbered alike.

A fenestrated rod or plate 108 is secured to each corresponding vertebrae 102–105 by a respective loop of cable 110–113. Each such cable has a top tie portion 114 that is secured to the fenestrated rod or plate 108, a superior-vertebral-notch portion 115, a spinal canal portion 116, an inferior-vertebral-notch portion 117, and a bottom-tie portion 118. If the cables 110–113 comprise single-strand wire, the top and bottom tie portions 114 and 118 may be secured by twisting them together. If the cables 110–113 comprise multi-strand cable, the top and bottom tie portions 114 and 118 may be secured by crimps and/or collets.

The fenestrated rod or plate 108 is constructed in one embodiment with a flat-bar stock having a series of cable holes. Such holes are spaced apart and occur at intervals that suit good cable anchor deployment. In other embodiments it is a metal rod with many transverse holes drilled through.

The approach and departure angles of cable portions 115 and 117 are preferably set to minimize wiggle and slack between the vertebrae 102–105 and the fenestrated rod or plate 108. Preferred materials include surgical-grade stainless steel, titanium, and polyethylene. The flat-bar stock itself is preferably relieved of sharp edges on all corners and edges. The outside edges along the length may be necked together at a variety of strategic points to give clearance to posterior spinous processes.

The fenestrated rod or plate 108 is constructed in another embodiment with a rod stock having a series of clamp-on ears. Such ears have cable loop holes and are spaced apart on the rod to occur at intervals that suit good cable anchor deployment. Here too, the approach and departure angles of cable portions 115 and 117 are preferably set to minimize wiggle and slack between the vertebrae 102–105 and the fenestrated rod or plate 108. Preferred materials include surgical-grade stainless steel, titanium, and polyethylene.

In FIG. 2, a spinal-fixation system 200 comprises a symmetrical pair of bridgings 202 and 204 that lie along a posterior length of a portion of the spine of a patient between spinous processes. A set of respective cables, represented by left and right cables 206 and 208, secure the bridgings 202 and 204 to a corresponding thoracic, lumbar, or cervical vertebrae 210. Such spinal-fixation system 200 is similar to the spinal-fixation system 100 of FIG. 1, and is shown here in cross-section to better illustrate the intended use. The cables 206 and 208 pass through a dorsal corner or sublaminar space of a spinal canal area 212 posterior to a spinal cord 214. A disc 216 is shown anterior to the spinal canal area 212.

FIGS. 3A and 3B represent a spinal-fixation system embodiment of the present invention, and is referred to herein by the general reference numeral 300. The system 300 includes a smooth rod 302 that functions like the fenestrated rod or plate 108 in FIG. 1. A cable 304 is the equivalent of cables 110–113 in FIG. 1, and is used to secure the rod 302 directly, e.g., to vertebrae 102–105 in FIG. 1 and vertebrae 210 in FIG. 2. The rod 302 has a number of tapered holes 306 that each capture a pair of collet halves 308 and 310. Many such tapered holes can be disposed all along the length of the rod to give the surgeon ample choices for optimum cable anchoring angles.

FIG. 3A shows the collet halves 308 and 310 disassembled, as before installation. FIG. 3B shows them locked into the tapered hole 306 by virtue of mutual friction with cable 304 and a tension applied to it. In some applications, it is preferable to snip off any excess loose-ends of the cable 304. In alternative embodiments of the present invention, it is preferable to capture the collet halves 308 and 310 inside the tapered hole 306 with a snap-ring. This would simplify the job of the surgeon by eliminating small loose pieces, and the cable could be simply pushed through one-way to be locked-in. A tensioner and cable-cutter would be used for final adjustment.

FIG. 4 illustrates a spinal-fixation system embodiment of the present invention, and is referred to herein by the general reference numeral 400. It is similar to systems 100, 200, and 300. A fenestrated support rod 402 is shown with a single cable loop 404 that represents any number of such loops attached to a single rod. Other cable loops can also be included at other radial angles to band-capture spinous processes to the left or right, as well as looping through the spinal canal as shown in FIGS. 1A, 1B, and 2. A pair of collets 406 and 408 lock the cable tightly into the rod 404. Crimps or set-screws could also be used.

Figure 5A:
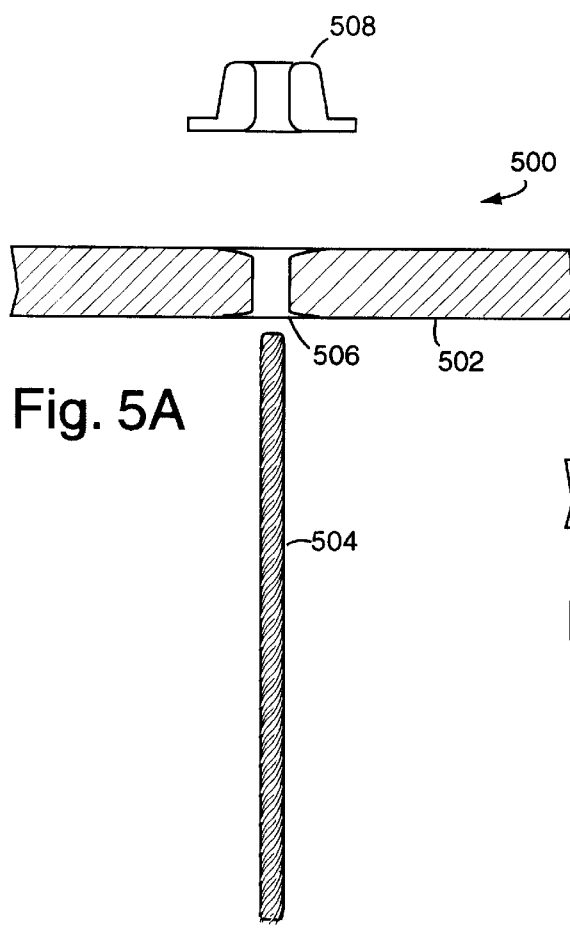
FIGS. 5A and 5B are partial cross-sectional diagrams of an embodiment of the present invention that attaches anchoring cables with crimps.
Figure 5B:
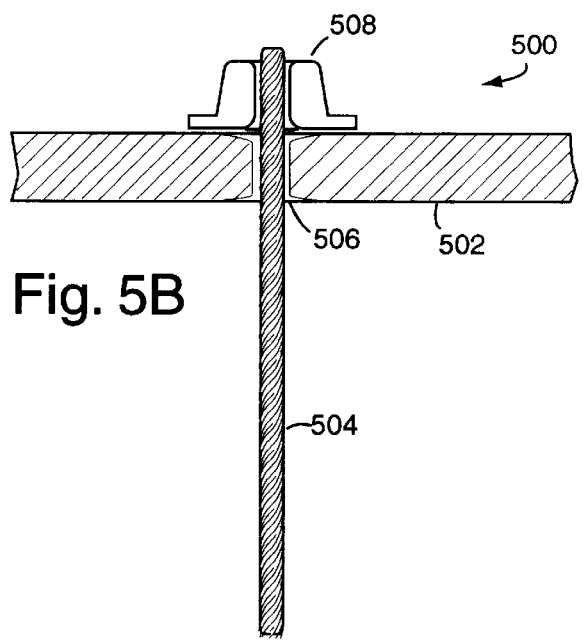

FIGS. 5A and 5B represent a spinal-fixation system embodiment of the present invention, and is referred to herein by the general reference numeral 500. The system 500 includes a fenestrated rod 502. An anchoring cable 504 is used to immobilize each involved vertebrae (e.g., vertebrae 102–105 in FIG. 1 and vertebrae 210 in FIG. 2) through a hole 506. Many such holes 506 can be disposed all along the length of the rod 502 to give the surgeon ample choices for optimum cable anchoring angles. A crimp 508 is used at each cable end.

FIG. 5A shows the various pieces disassembled, as before installation. FIG. 5B shows them assembled. In some applications, it is preferable to snip off any excess loose-ends of the cable 504. A conventional tensioner and cable-cutter can be used for final adjustment.

Figure 6:
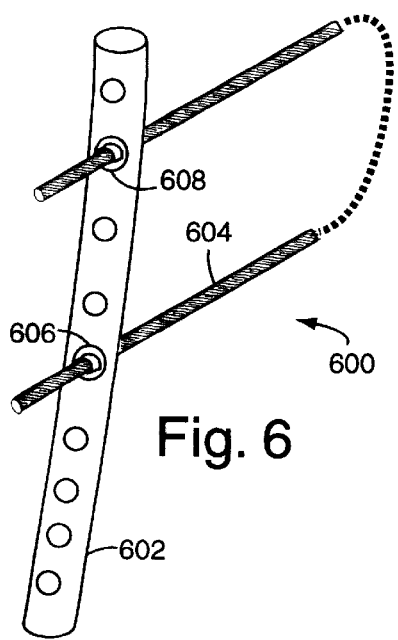
FIG. 6 is a perspective diagram of a spinal fixation system similar to that of FIGS. 5A and 5B.

FIG. 6 illustrates a spinal-fixation system embodiment of the present invention, and is referred to herein by the general reference numeral 600. It is similar to systems 100, 200, and 300. A fenestrated support rod 602 is shown with a single cable loop 604 representative of any number of such loops attached to a single rod. Other cable loops can also be included at other radial angles to band-capture spinous processes to the left or right, as well as looping through the spinal canal as shown in FIGS. 1A, 1B, and 2. A pair of cable crimps 606 and 608 lock the cable tightly into the rod 604.

Figure 7:
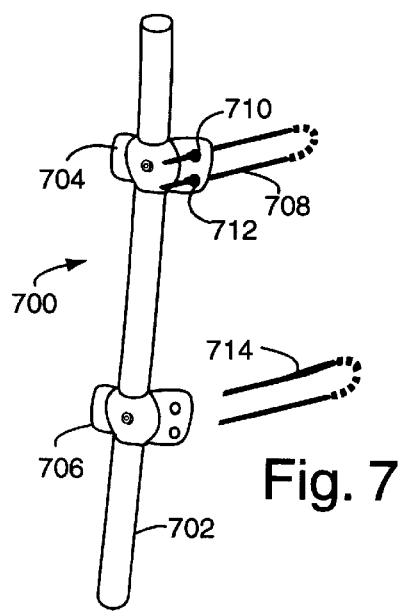
FIG. 7 is an assembly diagram of a spinal fixation system in an alternative embodiment of the present invention that uses a smooth rod and cable anchors.

FIG. 7 illustrates a spinal-fixation system embodiment of the present invention, and is referred to herein by the general reference numeral 700. It is similar to systems 100, 200, 300, and 600. A smooth rod 702 with no cable-holes of its own has a number of cable anchors, represented by cable anchors 704 and 706. These can be positioned anywhere along the smooth rod 702 and locked into position with set-screws or clamps. A cable 708 is looped around a vertebrae that is involved in a spinal immobilization procedure. The loose ends of cable 708 are passed through two holes provided and cinched with crimps 710 and 712, or other suitable clips or connectors. A cable 714 is shown before being installed into the cable anchor 706.

Although particular embodiments of the present invention have been described and illustrated, such is not intended to limit the invention. Modifications and changes will no doubt become apparent to those skilled in the art, and it is intended that the invention only be limited by the scope of the appended claims.

What is claimed is:

1. A spinal-fixation system, comprising:

a trans-vertebral bridging for spanning at least two vertebrae longitudinal to a human spine;

a series of anchor holes disposed along a length of the bridging; and a plurality of cables individually looped around said at least two vertebrae and terminated in respective ones of the series of anchor holes;

wherein, a system for immobilizing said spine is provided.

2. The system of claim 1, wherein:

the trans-vertebral bridging comprises two approximately parallel parts for placement between spinous processes of said vertebrae on left and right posterior sides.

3. The system of claim 1, wherein:

the trans-vertebral bridging comprises flat bar parts for placement between spinous processes of said vertebrae on left and right posterior sides.

4. The system of claim 1, wherein:

the trans-vertebral bridging comprises smooth rods for placement between spinous processes of said vertebrae on left and right posterior sides.

5. The system of claim 1, wherein:

the cables provide loops for passing through a dorsal corner of a spinal canal area of each corresponding vertebrae.

6. The system of claim 1, wherein:

the series of anchor holes are strategically located along a length of the bridging to minimize wiggle and slack between said vertebrae.

7. The system of claim 1, further comprising:

a collet for locking a respective one of the cables into a corresponding one of the series of anchor holes.

8. The system of claim 7, wherein:

the collets are split in two to provide a gripping action on the cables.

9. The system of claim 8, wherein:

the series of anchor holes are each such that they are tapered to generate said gripping action when the cables are under tension.

10. The system of claim 9, wherein:

the series of anchor holes further include a retainer to capture the collets.

11. A spinal-fixation system, comprising:

a smooth rod for spanning at least two vertebrae longitudinal to a human spine and including no holes;

a plurality of cable anchors disposed along a length of the smooth rod, and configured to be able to slip along the length of the smooth rod, and further including a number of anchor-cable holes;

a plurality of cables provided for looping around said at least two vertebrae and terminated in respective ones of said number of anchor-cable holes;

a locking fastener for fixing each of the plurality of cable anchors to the smooth rod; and a number of connectors respectively disposed to secure each of the plurality of cables to corresponding ones of the plurality of cable anchors;

wherein, the system provides for an immobilization of said at least two vertebrae.

* * * * *